United States Patent
Najafi

(10) Patent No.: US 10,687,709 B2
(45) Date of Patent: Jun. 23, 2020

(54) IMPLANTABLE SENSING DEVICES AND ANCHORING METHODS THEREFOR

(71) Applicant: Integrated Sensing Systems, Ypsilanti, MI (US)

(72) Inventor: Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 205 days.

(21) Appl. No.: 15/805,969

(22) Filed: Nov. 7, 2017

(65) Prior Publication Data

US 2018/0116516 A1 May 3, 2018

Related U.S. Application Data

(63) Continuation-in-part of application No. 15/591,087, filed on May 9, 2017.

(60) Provisional application No. 62/391,742, filed on May 9, 2016, provisional application No. 62/391,743, filed on May 9, 2016, provisional application No. 62/604,516, filed on Jul. 10, 2017.

(51) Int. Cl.
*A61B 5/00* (2006.01)
*A61B 5/0215* (2006.01)
*A61B 5/021* (2006.01)

(52) U.S. Cl.
CPC .......... *A61B 5/0031* (2013.01); *A61B 5/0215* (2013.01); *A61B 5/6882* (2013.01); *A61B 5/02141* (2013.01); *A61B 5/6869* (2013.01); *A61B 2560/063* (2013.01)

(58) Field of Classification Search
None
See application file for complete search history.

(56) References Cited

U.S. PATENT DOCUMENTS

| | | |
|---|---|---|
| 2002/0077555 A1 | 6/2002 | Schwartz |
| 2002/0120200 A1 | 8/2002 | Brockway et al. |
| 2006/0187044 A1 | 8/2006 | Fabian et al. |

(Continued)

FOREIGN PATENT DOCUMENTS

| | | |
|---|---|---|
| EP | 0989384 A2 | 3/2000 |
| WO | WO 2016131020 A1 | 8/2016 |

OTHER PUBLICATIONS

European Search Report for European Application No. 17210340.0, dated Jan. 21, 2019, 16 pages.

*Primary Examiner* — Ankit D Tejani
(74) *Attorney, Agent, or Firm* — Hartman Global IP Law; Gary M. Hartman; Domenica N. S. Hartman

(57) ABSTRACT

Implantable wireless sensor assemblies and methods for monitoring physiological parameters within living bodies. Such sensor assembly includes a sensing device with a housing having an internal cavity, a transducer and electrical circuitry within the cavity, and an antenna that is within the cavity or outside the housing. The sensor assembly further includes a housing portion in which the transducer, the electrical circuitry, and the antenna are not located, and anchoring elements for securing the sensing device within a living body. The housing portion is separately formed and directly attached to a distal end of the housing, or is integrally formed as a discrete region of the housing at the distal end thereof. The anchor elements surround a coupling feature of the housing portion but does not surround the transducer or the antenna of the sensing device.

11 Claims, 14 Drawing Sheets

(56) References Cited

U.S. PATENT DOCUMENTS

2009/0005656 A1\* 1/2009 Najafi ................ A61B 5/6882
  600/301
2013/0144379 A1\* 6/2013 Najafi ................ A61B 5/0024
  623/2.11

\* cited by examiner

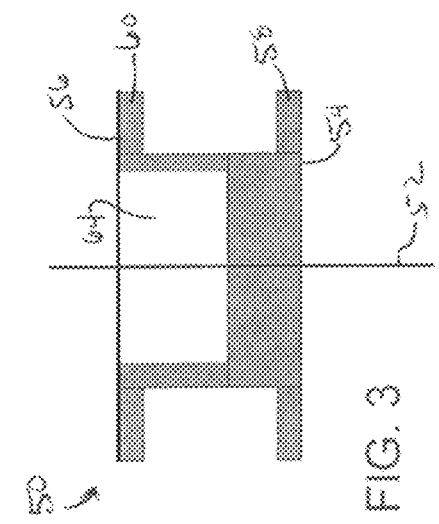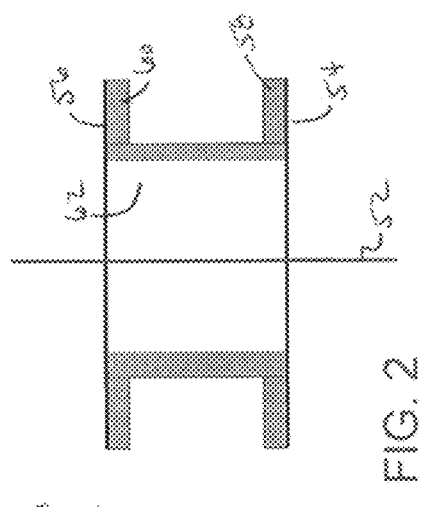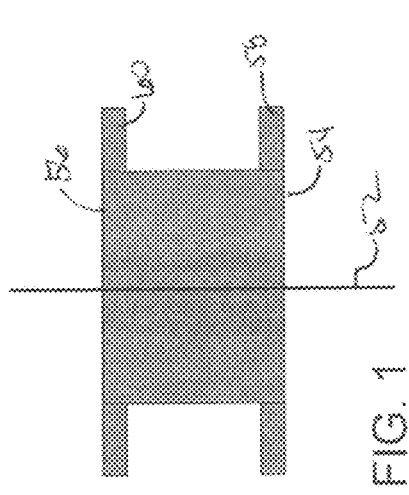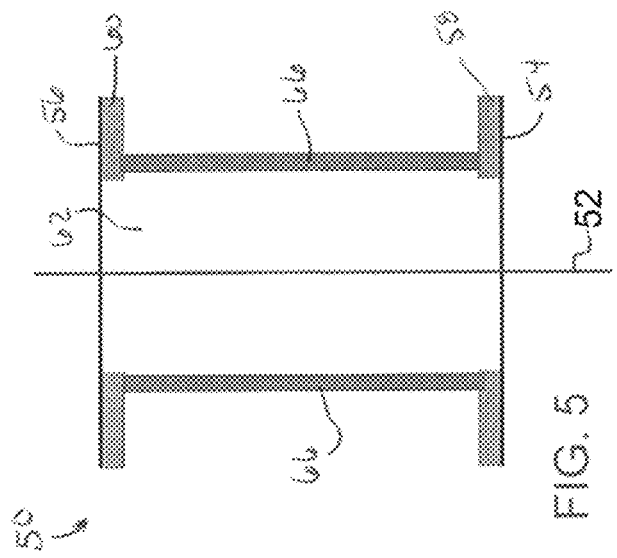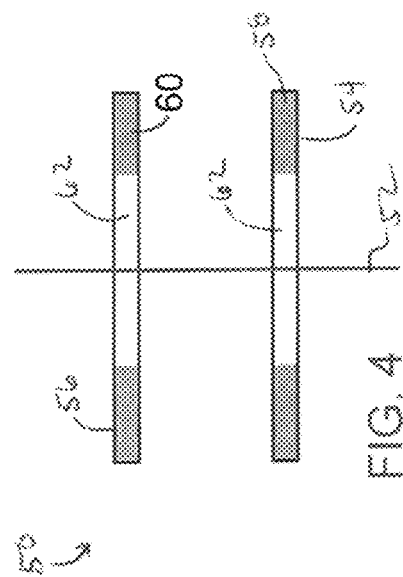

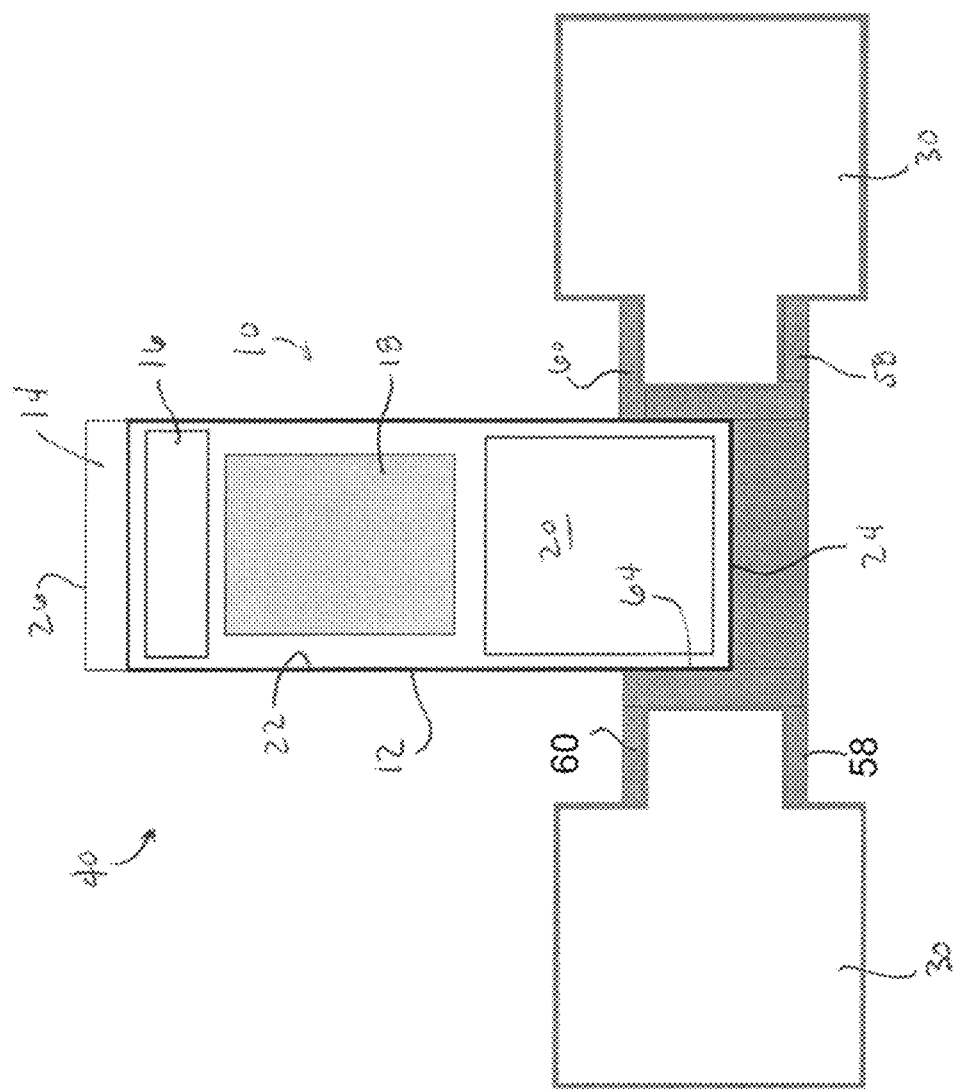

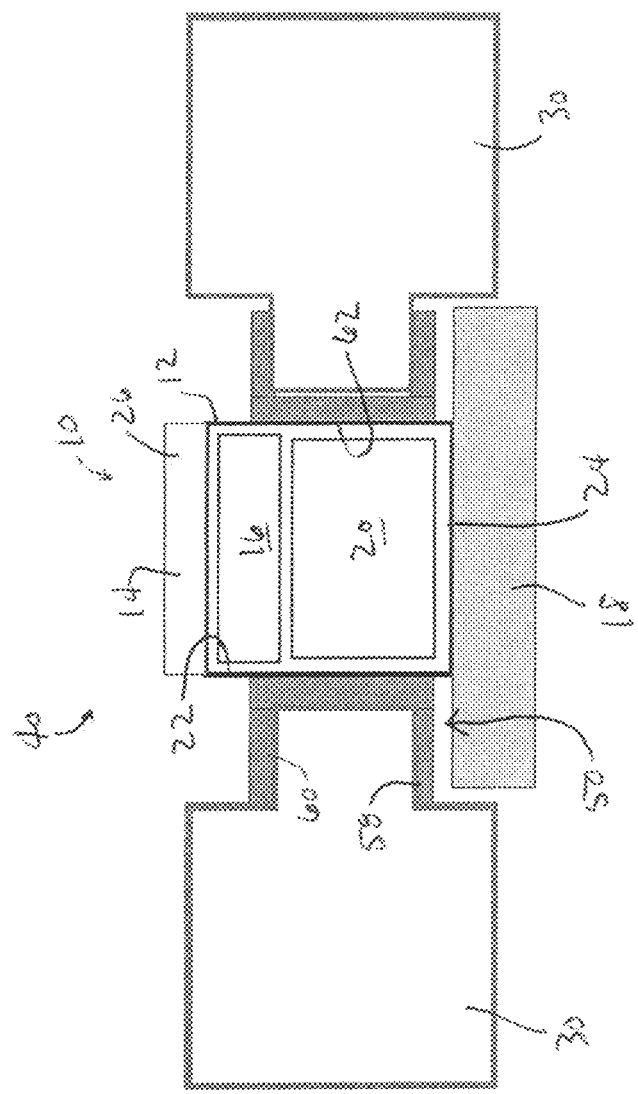

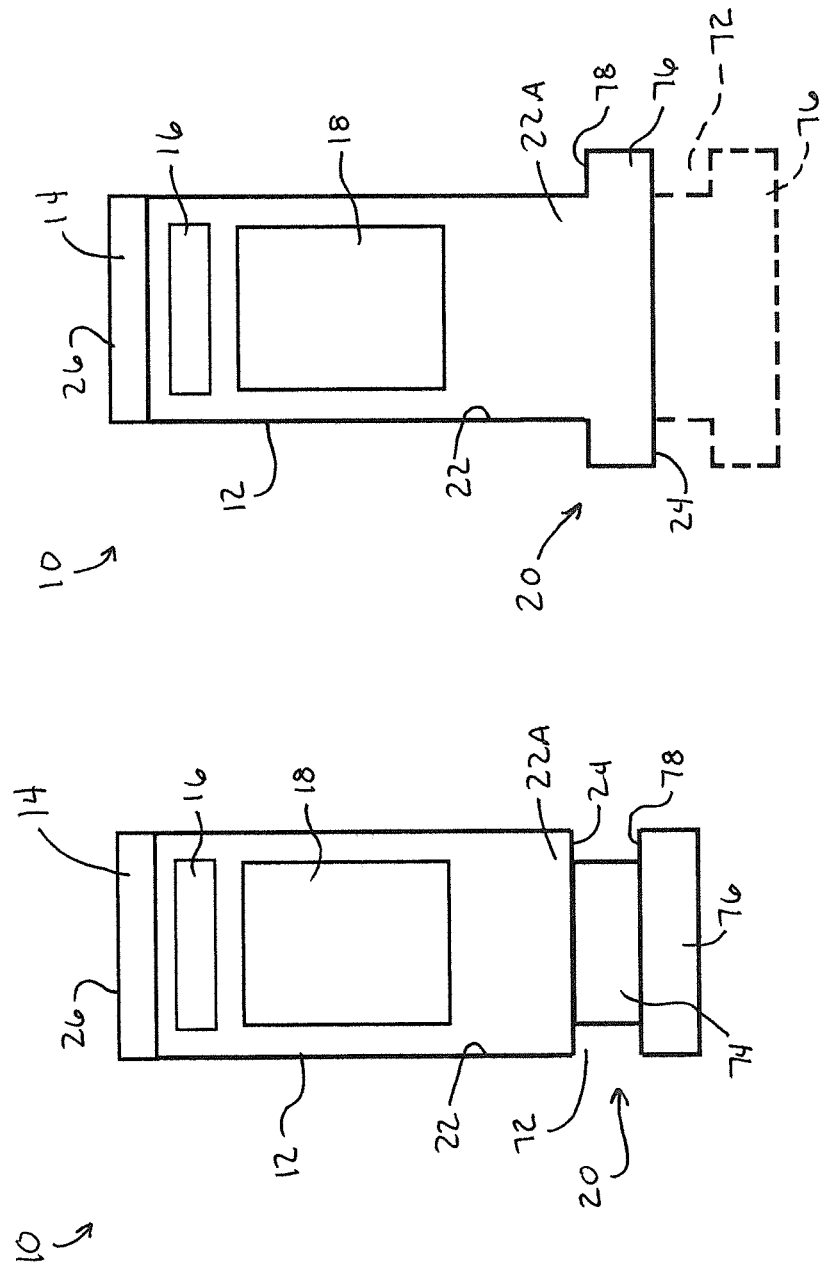

IMPLANTABLE SENSING DEVICES AND ANCHORING METHODS THEREFOR

CROSS REFERENCE TO RELATED APPLICATIONS

This is a continuation-in-part patent application of co-pending U.S. patent application Ser. No. 15/591,087 filed May 9, 2017, which claims the benefit of U.S. Provisional Application No. 62/391,742, filed May 9, 2016. This application also claims the benefit of U.S. Provisional Application No. 62/604,516 filed Jul. 10, 2017. The contents of these prior applications are incorporated herein by reference.

Various patents pertain to procedures, systems, and implantable sensing devices suitable for monitoring physiological parameters within living bodies, as nonlimiting examples, U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. Some of the inventions disclosed in these patents particularly pertain to anchoring and delivery of implantable wireless hermetically-sealed sensing devices by percutaneous methods or minimally invasive surgery (MIS). While the innovations disclosed in these patents can be applied to many different body organs and systems, of particular interest has been placement in the cardiovascular system and especially within or in the vicinity of a heart chamber to monitor one or more physiological parameters within the chamber.

Some of the inventions disclosed in the above-noted patents note the ability of using metallic devices, for example vascular closure devices, atrial septum defect occluder devices (ASD and PFO occluders), and closure paravalvular leak devices, to anchor implantable wireless sensing devices. Nonlimiting examples of such devices include the CELT ACD® produced by Vasorum Ltd. (http://vasorum.ie/) or various devices produced by Occlutech International AB (http://www.occlutech.com/index.php/en/products). However, various problems can be encountered when attempting to anchor an implantable wireless sensing device using such devices, for example, metallic vascular closure devices can have a Faraday-cage effect on a wireless sensing device that can adversely affect the range and quality of tele-powering or wireless communications of the sensing device, and stresses induced in the sensing device caused by its attachment to the closure device can adversely affect the performance of the sensing device, for example, by inducing drift.

BACKGROUND OF THE INVENTION

The present invention generally relates to procedures, implantable wireless sensing devices, and sensor assemblies suitable for monitoring physiological parameters within living bodies.

According to one aspect of the invention, a sensor assembly includes a sensing device comprising a housing having at least one internal cavity, a transducer and electrical circuitry within the at least one internal cavity, and an antenna that is within the at least one internal cavity or outside the housing. The transducer is located at a proximal end of the housing opposite a distal end of the housing. The sensor assembly further includes a housing portion in which the transducer, the electrical circuitry, and the antenna are not located, and anchoring means for securing the sensing device within a living body. The housing portion is separately formed and directly attached to a distal end of the housing, or is integrally formed as a discrete region of the housing at the distal end thereof. The anchor means surrounds a coupling means of the housing portion but does not surround the transducer or the antenna of the sensing device so that a metal portion of the anchor means is sufficiently remote from the transducer and the antenna to not interfere with operations thereof.

Other aspects of the invention include methods of using the sensor assembly to sense a physiological parameter of a living being and as a closure or occluder device.

Other aspects and advantages of this invention will be better appreciated from the following detailed description.

BRIEF DESCRIPTION OF THE DRAWINGS

FIGS. 1 through 5 schematically represent anchors of types that can be used to anchor implantable wireless sensing devices in accordance with nonlimiting embodiments of the invention.

FIGS. 12 through 20 schematically represent various sensor assemblies comprising the anchors of FIGS. 1 through 5 and the sensing devices of FIGS. 7 through 11 in accordance with nonlimiting aspects of the invention.

FIGS. 21 and 22 schematically represent additional sensing devices in accordance with nonlimiting aspects of the invention, wherein the devices incorporate, respectively, a discrete attachment or an integral housing portion by which the devices can be coupled to an anchor and/or anchor interface member therefor.

DETAILED DESCRIPTION OF THE INVENTION

Figure 6:
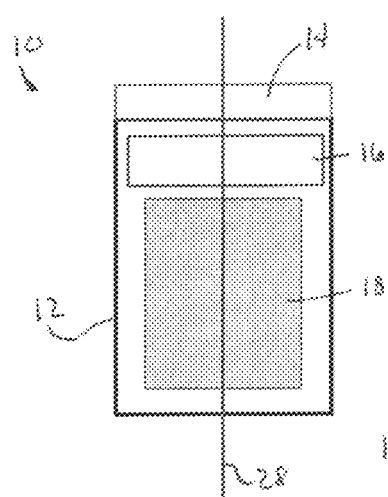
FIG. 6 schematically represents a conventional sensing device.

Illustrated in the drawings are components of monitoring systems that include the implementation of an implantable wireless sensing device configured to be placed within a living body, including internal organs thereof, for monitoring one or more physiological parameters. Physiological parameters of particular interest include but are not limited those relating to the function of the circulatory, respiratory, urinary, and nervous systems, and organs of particular interest include but are not limited to the heart, blood vessels, liver, brain (e.g., intracranial), kidneys, lungs, and bladder. Notable particular examples relating to the heart include any of the four heart chambers (particularly the left ventricle and left atrium), and notable examples relating to blood vessels include the inferior vena cava and blood vessels associated with the heart and lungs.

There are also advantageous aspects relating to the placement of an implantable sensing device, such as an IHM sensor or other type of sensor, in the inferior vena cava. The largest vein in the human body, the inferior vena cava collects blood from veins serving the tissues inferior to the heart and returns this blood to the right atrium of the heart. Although the vena cava is very large in diameter, its walls are thin due to the low pressure exerted by venous blood. The inferior vena cava forms at the superior end of the pelvic cavity when the common iliac veins unite to form a larger vein. From the pelvis, the inferior vena cava ascends through the posterior abdominal body wall just to the right of the vertebral column. Along its way through the abdomen, blood from the internal organs joins the inferior vena cava through a series of large veins, including the gonadal, renal, suprarenal and inferior phrenic veins. Blood from the tissues of the lower back, including the spinal cord and muscles of the back, enters the vena cava through the lumbar veins. Many smaller veins also provide blood to the vena cava from the tissues of the abdominal body wall. Upon reaching the heart, the inferior vena cava connects to the right atrium on its posterior side, inferior to the connection of the superior vena cava. The inferior vena cava and its tributaries drain blood from the feet, legs, thighs, pelvis and abdomen and deliver this blood to the heart. Many one-way venous valves help to move blood through the veins of the lower extremities against the pull of gravity. Blood passing through the veins is under very little pressure and so must be pumped toward the heart by the contraction of skeletal muscles in the legs and by pressure in the abdomen caused by breathing. Venous valves help to trap blood between muscle contractions or breaths and prevent it from being pulled back down towards the feet by gravity.

Preferred aspects of the present invention include the ability to provide implantable wireless sensing devices suitable for monitoring one or more physiological parameters within blood vessels, including those mentioned above. The physical footprint of such an implantable wireless sensing device is preferably limited to the sensing device, an anchor that secures the sensing device to or within the vein, and optionally a separate antenna that wirelessly transmits data and other communications to a remote device, such as a readout unit, which may also tele-power the sensing device. The physical footprint of such an implantable wireless sensing device can be far smaller than monitoring systems that must be physically connected to a relatively large remote transmitting device, for example, as in the case of the LVP-1000 Left Ventricle Pressure Monitoring System offered by Transoma Medical, Inc. Implantable wireless sensing device utilized by the invention may employ resonant, passive, or active communication schemes described in prior patents, including but not limited to those disclosed in U.S. Pat. Nos. 8,744,544, 8,715,300, 8,696,693, 8,512,252, 8,322,346, 8,267,863, 8,014,865, 7,860,579, 7,686,762, 7,634,319, 7,615,010, 7,317,951, and 6,968,743. The drawings schematically represent various implantable wireless sensing devices as comprising a single hermetically-sealed housing that contains a transducer and electronic circuitry, for example, an application specific integrated circuit (ASIC), which operate in combination with an antenna to transmit and receive data.

In the drawings, the antenna is represented as comprising a coil (e.g., copper windings) wrapped around a core (e.g., ferrite), though other antenna configurations and materials are foreseeable. The transducer, which is located at a proximal end of the housing, is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. The transducer is adapted to sense a physiological parameter of a living being. A particular but nonlimiting example of a suitable transducer for hemodynamic monitoring of various blood pressures within the cardiovascular system is a MEMS capacitive pressure sensor for sensing pressure, though other materials and any variety of sensing elements, e.g., capacitive, inductive, resistive, piezoelectric, etc., could be used. For example, the transducer could be configured to sense temperature, flow, acceleration, vibration, pH, conductivity, dielectric constant, and chemical composition, including the composition and/or contents of a biological fluid, for example, oxygen, carbon dioxide, glucose, gene, hormone, or gas content of the fluid.

The sensing device may be powered with a battery or other power storage device, but in preferred embodiments is powered entirely by a remote device that is not configured for implantation, such as a readout unit. Such a readout unit may be configured to receive an output signal from the sensing device, process the signal, and relay the processed signal as data in a useful form to a user. Because the sensing device is equipped with a built-in antenna, the device requires only an anchor for implantation and does not require a wire, cable, tether, or other physical component that conducts the output of the sensing device to a separate location where another component utilizes the output of the sensing device and/or transmits the output of the sensing device to a location outside the body of the patient.

In the drawings, consistent reference numbers are used to identify functionally equivalent structures of various implantable wireless sensing devices 10 and to identify functionally equivalent structures of various anchors 50 that are adapted to secure the sensing devices 10. As noted above, the drawings schematically represent the sensing devices 10 as comprising a single hermetically-sealed housing 12 that contains a transducer 14 and electronic circuitry 16, for example, an application specific integrated circuit (ASIC), which operate in combination with an antenna 18 to transmit and receive data. The sensing devices 10 differ from each other by the placement of the antenna 18 within or outside the housing 12. The anchors 50 may be chosen in part on the basis of the placement of the antenna 18 relative to the housing 12. The housings 12 of the sensing devices 10 are configured to comprise a housing portion 20 that is in addition to portions of the housing 12 in which one or more internal cavities 22 are located that contain the transducer 14 and antenna 18. As such, the additional housing portion 20 is not required to contain, and preferably does not contain, any component relating to the operation of the transducer 14 and the transmission of data to and from the sensing device 10 via the antenna 18, and therefore a cavity is not required to be present in the additional housing portion 20. Furthermore, such an additional housing portion 20 may form a distal end 24 of the housing 12, i.e., opposite of the proximal end 26 of the housing 12 where the transducer 14 is located such that the antenna 18 is located between the transducer 14 and the additional housing portion 20, or may be located between the transducer 14 and the antenna 18, or may be a combination of both (i.e., the additional housing portion 20 may comprise two spaced-apart portions 20) that are connected together only through the housing 12 or by the anchor 50. The additional housing portion 20 may be integrally formed as an indiscrete region of the housing 12, or separately formed and directly attached to the housing 12, or separately formed and indirectly attached to the housing 12 with the anchor 50.

Instead of containing components relating to the operations of the transducer 14 and antenna 18 or to data transmission, the additional housing portion 20 can be dedicated to the attachment of an anchor 50 to the sensing device 10. In particular, the additional housing portion 20 is particularly well suited for enabling the sensing device 10 to be secured with metallic anchors 50, including but not limited to vascular closure devices, atrial septum defect occluder devices (ASD and PFO occluders), and closure paravalvular leak devices, such that the transducer 14 and antenna 18 are sufficiently remote from the anchor 50 that metallic portions of the anchor 50 do not interfere with their operations. As an example, the additional housing portion 20 preferably creates a spacial axial distance between the antenna 18 and a metallic anchor 50 (or metallic portions thereof) to reduce Faraday-cage effects otherwise caused by metal, and creates a spacial axial distance between a metallic anchor 50 and the transducer 14 to reduce if not avoid stresses that could mechanically interfere with the operation of the transducer 14, for example, cause a drift in its signal output.

The attachment of the sensing device 10 to the anchor 50 can be accomplished in different ways, including but not limited to one or more of the following: attachment by a third material (e.g., glue, epoxy, etc.), mechanical grips, threads (e.g., the housing 12 is threaded into the anchor 50), using a discrete attachment member (e.g., made from PEEK or NiTi material), compression, thermal compression, or a mechanical attachment feature of the sensing device 10 or anchor 50 (e.g., fingers, loops, spirals, etc.).

FIGS. 1 through 5 schematically represent anchors 50 that have a generally cylindrical outline and define an axis 52 that may be an axis of rotational symmetry. Each of the anchors 50 has distal and proximal ends 54 and 56, at which axial spaced flanges or rings 58 and 60 are present. The anchors 50 are solid between their distal and proximal ends 54 and 56, i.e., lack an internal hole or cavity (FIG. 1), or have a through-hole 62 (FIG. 2), or have a blind hole 64 (FIG. 3), or comprise two discrete rings 58 and 60 that are not connected to each other but define two separate through-holes 62 (FIG. 4), or comprise two discrete rings 58 and 60 that are interconnected to each other by longitudinal legs 66 to define a through-hole 62 within the anchor 50 (FIG. 5). In the embodiments of FIGS. 2 through 5, the anchors 50 are sized to accommodate a sensing device 10 within their respective through-hole 62, blind hole 64, rings 58 and 60, and/or legs 66. In the embodiment of FIG. 1, a sensing device 10 may be attached to either axial end 54 or 56 of the anchor 50. Other anchor 50 configurations are also within the scope of the invention. The anchors 50 may be formed or fabricated from a variety of materials, including but not limited to metals including stainless steels and shape-memory alloys (e.g., NiTi alloys), polymers including PEEK, or combinations thereof.

FIGS. 6 through 11 schematically represent sensing devices 10 that each defines an axis 28 that may be an axis of rotational symmetry. The housings 12 of the sensing devices 10 are sized and shaped for attachment to one or more of the anchors 50 shown in FIGS. 1 through 5, for example, by attachment to either axial end 54 or 56 of the anchor 50 of FIG. 1, or placement in the through-hole 62, blind hole 64, rings 58 and 60, or legs 66 of the anchors 50 of FIGS. 2 through 5. The sensing device 10 of FIG. 6 will be referred to herein as a conventional sensing device 10, in that its housing 12 is represented as being sized to accommodate the transducer 14, antenna 18, and electronic circuitry 16 within an internal cavity 22 defined by the housing 12, with little additional cavity space not occupied by the transducer 14, antenna 18, and electronic circuitry 16. The sensing devices 10 of FIGS. 7 through 11 differ from the conventional sensing device 10 of FIG. 6 as well as from each other by the placement of the antenna 18 within (FIGS. 6 through 9 and 11) or outside (FIG. 10) their respective housings 12, and the inclusion of at least one additional housing portion 20 that is in addition to the internal cavity (or cavities) 22 that contain(s) the transducer 14, antenna 18, and electronic circuitry 16. The placement of the antenna 18 outside of the housing 12 in FIG. 10 allows for the diameter of the antenna 18 to be larger from the diameter of the housing 12. Because the diameter of the antenna 18 greatly affects the tele-powering and tele-communication range of the sensing device 10, the wider diameter antenna 18 of FIG. 10 may eliminate the requirement for a ferrite coil, so that the sensing device 10 requires only a coil.

Figure 7:
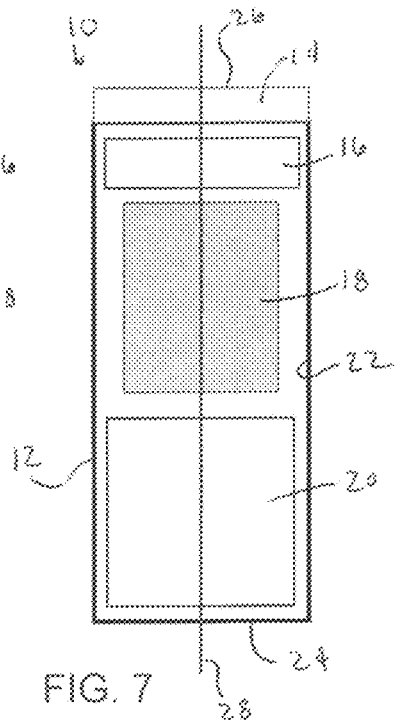
FIGS. 7 through 11 schematically represent sensing devices in accordance with nonlimiting aspects of the invention.
Figure 8:
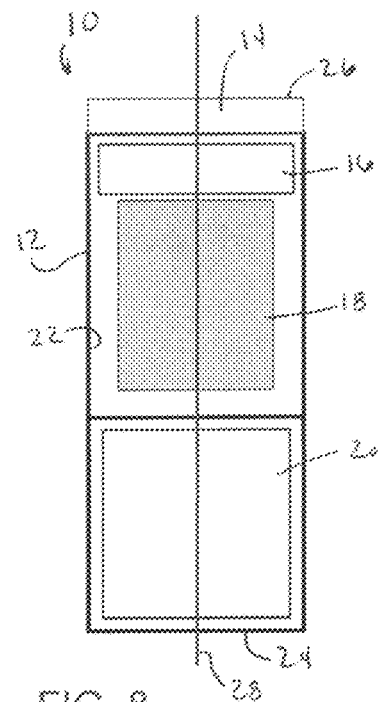
Figure 9:
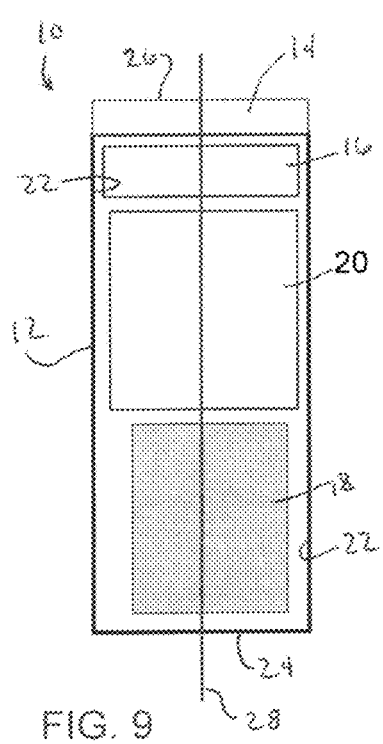
Figure 10:
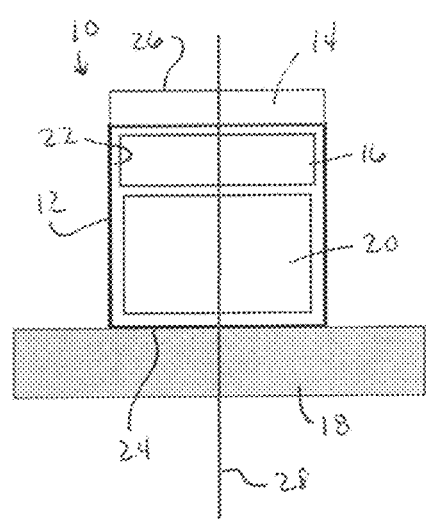
Figure 11:
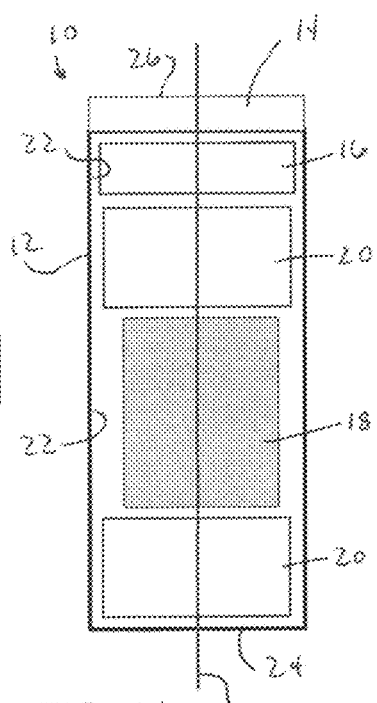

The additional housing portions 20 are not required to contain any component relating to the operation of the sensing device 10 or its transducer 14, antenna 18, or electronic circuitry 16, and therefore a cavity is not required to be present in the additional housing portions 20. As such, the representations of the additional housing portions 20 in the drawings do not necessarily (though may) indicate a cavity, but instead more generally indicate regions of their housings 12 that may entirely be a cavity-free solid. The additional housing portion 20 is represented in FIGS. 7 and 8 as located in or forming the distal end 24 of the housing 12 opposite its proximal end 26 where the transducer 14 and electronic circuitry 16 are located, such that the antenna 18 is located between the additional housing portion 20 and the transducer 14 and electronic circuitry 16. The additional housing portion 20 is represented in FIGS. 9 and 10 as located within a midsection of the housing 12 between the antenna 18 at the distal end 24 of the housing 12 and the transducer 14 and electronic circuitry 16 at the proximal end 26 of the housing 12. The additional housing portion 20 is represented in FIG. 11 as comprising two spaced-apart portions 20, a first between the antenna 18 located within the midsection of the housing 12 and the transducer 14 and electronic circuitry 16 at the proximal end 26 of the housing 12, and a second between the antenna 18 and the distal end 24 of the housing 12. The additional housing portions 20 of FIGS. 7 and 9 through 11 are integrally formed as an indiscrete region of the housing 12, whereas the additional housing portion 20 of FIG. 8 is separately formed and directly attached to the distal end 24 of the housing 12.

Figure 13:
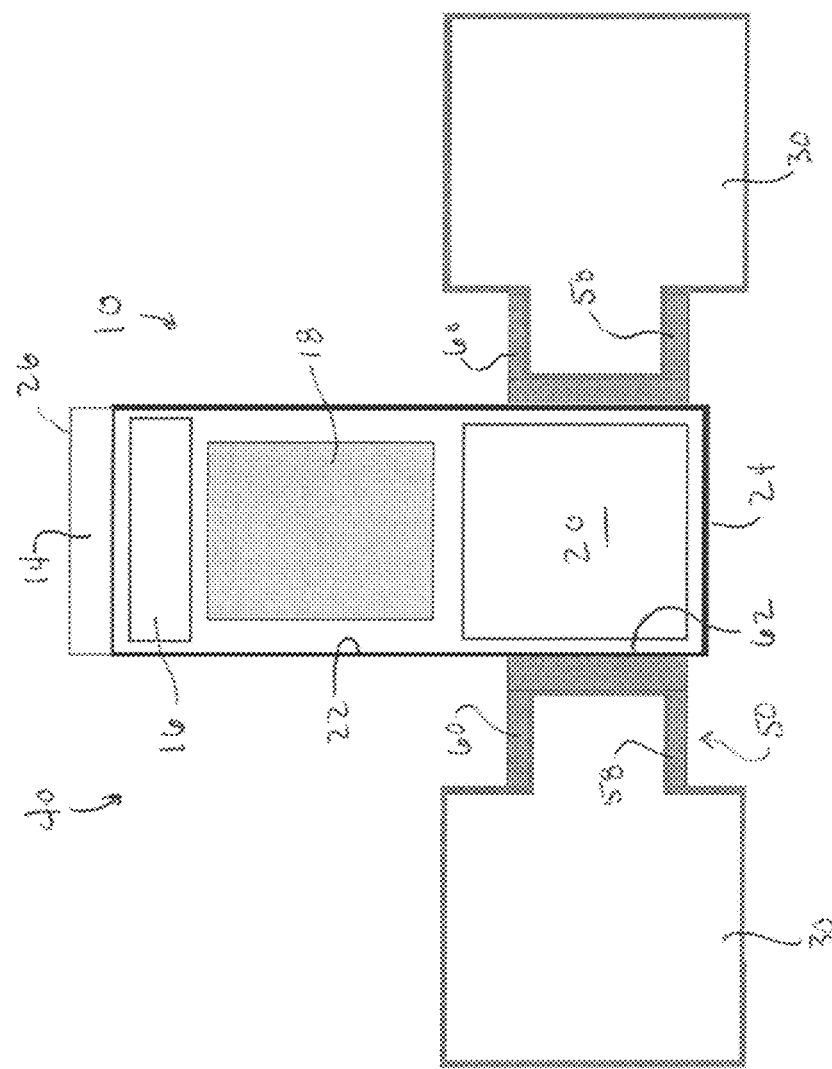
Figure 12:
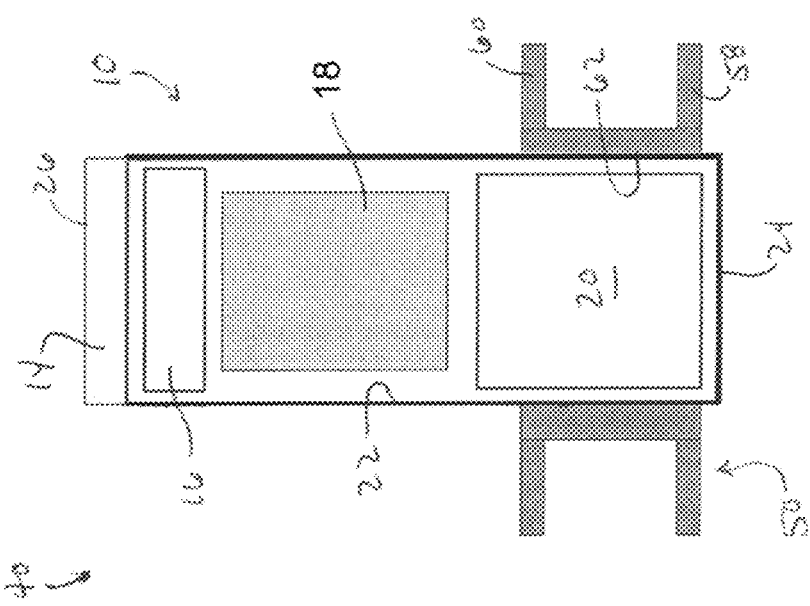

FIG. 12 represents a sensor assembly 40 comprising the sensing device 10 of FIG. 7 assembled with the anchor 50 of FIG. 2, and FIG. 13 represents the sensor assembly 40 of FIG. 12 implanted in a wall 30 of an organ such that the anchor 50 secures the sensing device 10 to the organ wall 30. As evident from FIG. 13, the distal end 24 of the sensing device 10 sufficiently extends through the through-hole 62 of the anchor 50 so that the anchor 50 contacts and surrounds or circumscribes only that part of the housing 12 that is formed by the additional housing portion 20 or otherwise in which the additional housing portion 20 is present, such that the anchor 50 does not have a negative effect or has a minimal negative effect on the functions of the internal antenna 18 and transducer 14. In FIGS. 12 and 13, the anchor 50 is radially aligned with the additional housing portion 20 with respect to the axis 28 of the housing 12 (FIG. 7).

Figure 15:
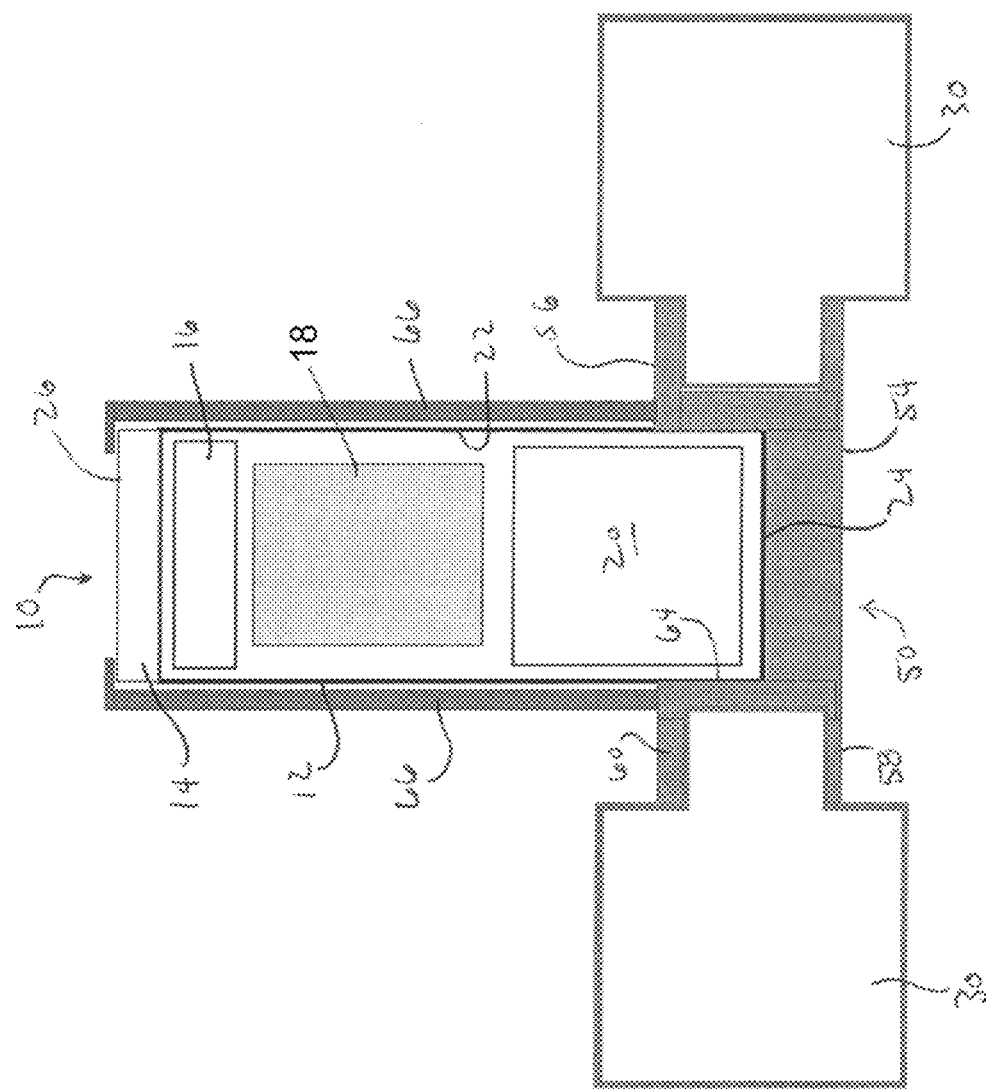

FIG. 14 represents a sensor assembly 40 comprising the sensing device 10 of FIG. 7 assembled with the anchor 50 of FIG. 3, and shows the sensor assembly 40 implanted in a wall 30 of an organ with the anchor 50. As evident from FIG. 14, the distal end 24 of the sensing device 10 is received in the blind hole 64 of the anchor 50 so that the anchor 50 contacts and surrounds or circumscribes only the distal end 24 of the housing 12, which is formed by or contains the additional housing portion 20. FIG. 15 represents a sensor assembly 40 similar to that of FIG. 14 but whose anchor 50 has been modified to have fingers or legs 66 that extend from the axial end 56 of the anchor 50 in which the blind hole 64 is formed and capture the proximal end 26 of the housing 12 to better secure the sensing device 10.

Figure 16:
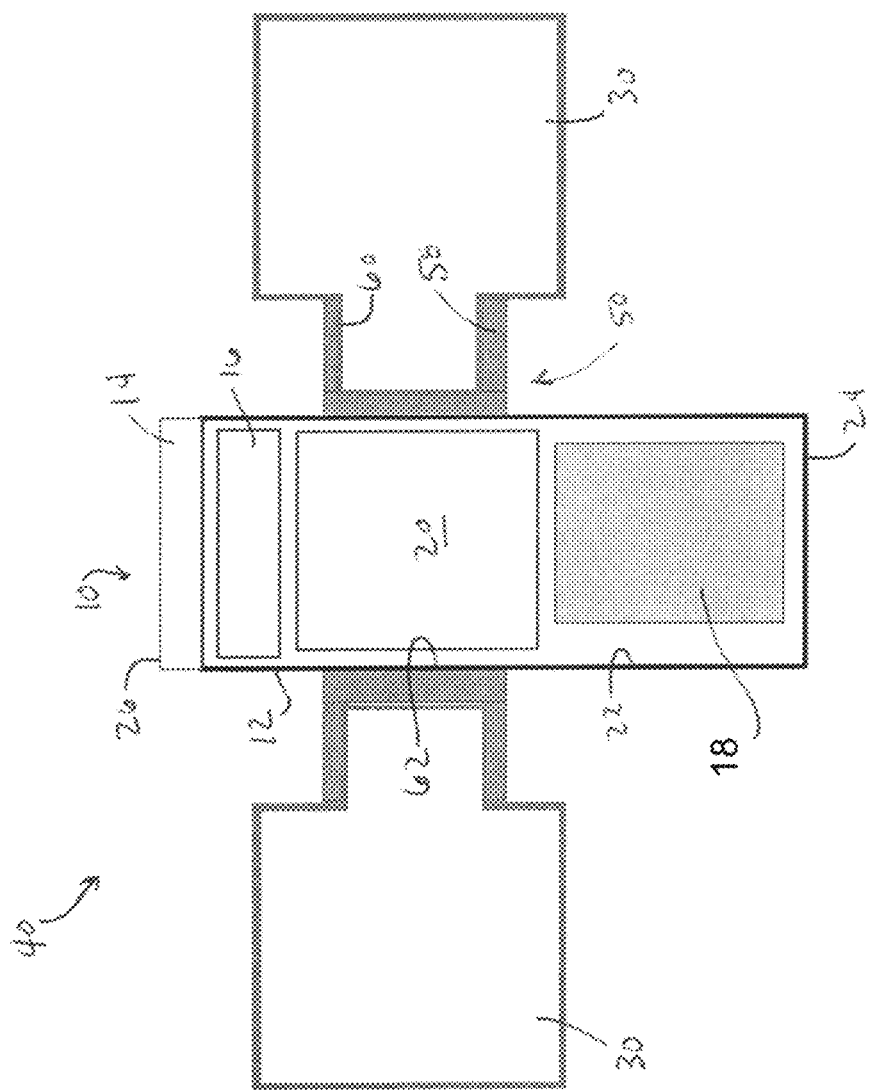

FIG. 16 represents a sensor assembly 40 comprising the sensing device 10 of FIG. 9 assembled with the anchor 50 of FIG. 2, and shows the sensor assembly 40 implanted in a wall 30 of an organ with the anchor 50. The distal and proximal ends 24 and 26 of the sensing device 10 are located outside of the through-hole 62 of the anchor 50, which contacts and surrounds or circumscribes only the midsection of the housing 12 that is formed by the additional housing portion 20 or otherwise in which the additional housing portion 20 is present. In FIG. 16, the anchor 50 is radially aligned with the additional housing portion 20 with respect to the axis 28 of the housing 12 (FIG. 9).

Figure 17:
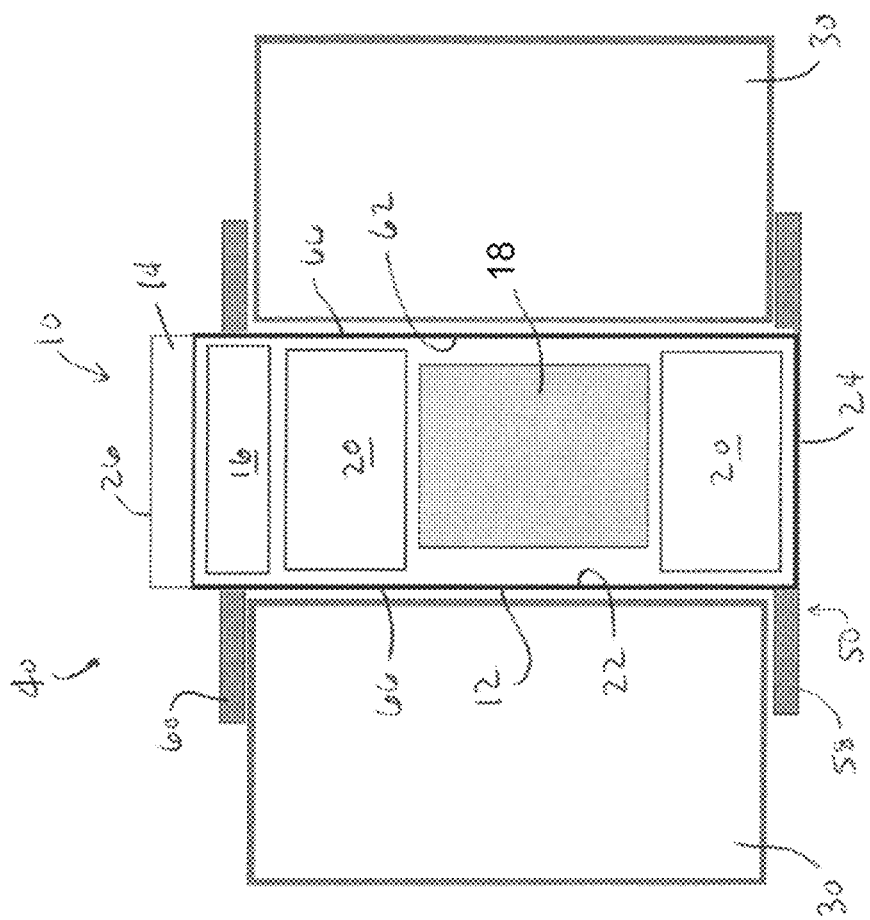
Figure 18:
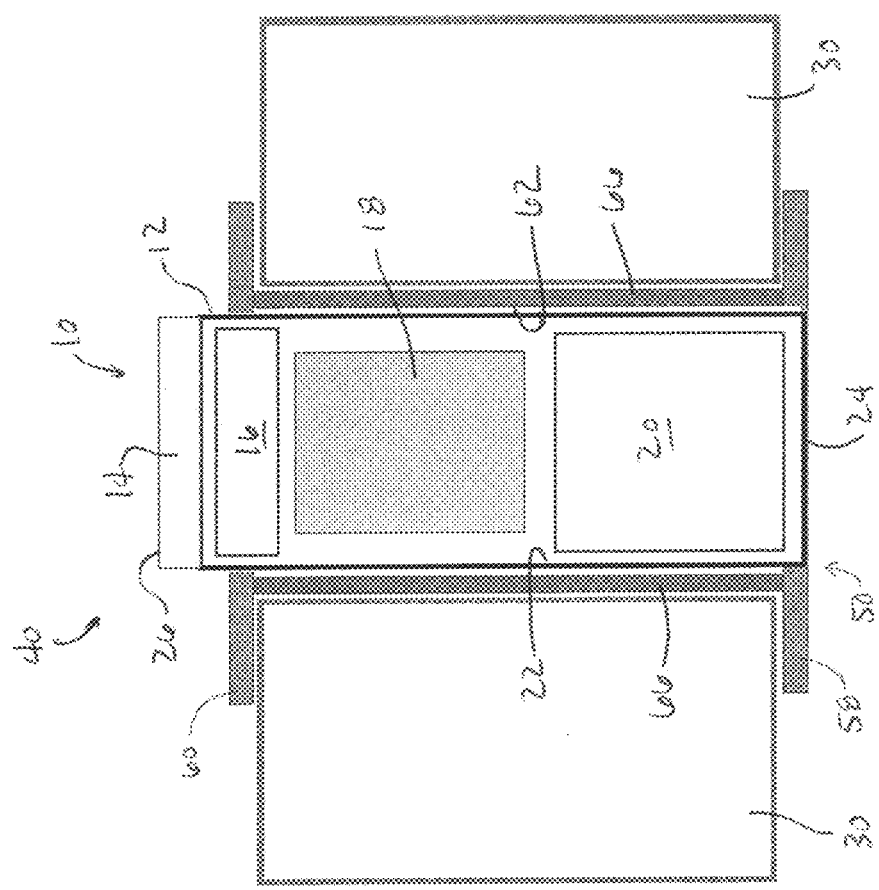

FIG. 17 represents a sensor assembly 40 comprising the sensing device 10 of FIG. 11 assembled with the anchor 50 of FIG. 5, and shows the sensor assembly 40 implanted in a wall 30 of an organ with the anchor 50. The distal and proximal ends 24 and 26 of the sensing device 10 are located at or adjacent opposite ends of the through-hole 62 of the anchor 50, which surrounds or circumscribes the housing 12 between its distal and proximal ends 24 and 26. As a result, the internal antenna 18 (located at the midsection of the housing 12) is not surrounded by either ring 58 and 60 of the anchor 50, but instead is only surrounded or circumscribed by the longitudinal legs 66 that interconnect the rings 58 and 60. In this embodiment, the rings 58 and 60 may be metallic, but the legs 66 are preferably formed of a nonmetallic material so as to not have a Faraday-cage effect on the antenna 18. FIG. 18 represents a sensor assembly 40 comprising the anchor 50 of FIG. 5 similar to FIG. 17, but assembled with the sensing device 10 of FIG. 7. The distal and proximal ends 24 and 26 of the sensing device 10 are again located at opposite ends of the through-hole 62 of the anchor 50, and the internal antenna 18 (located near the proximal end 26 of the housing 12) is only surrounded or circumscribed by the longitudinal legs 66 and is not surrounded by either ring 58 or 60.

Figure 19:
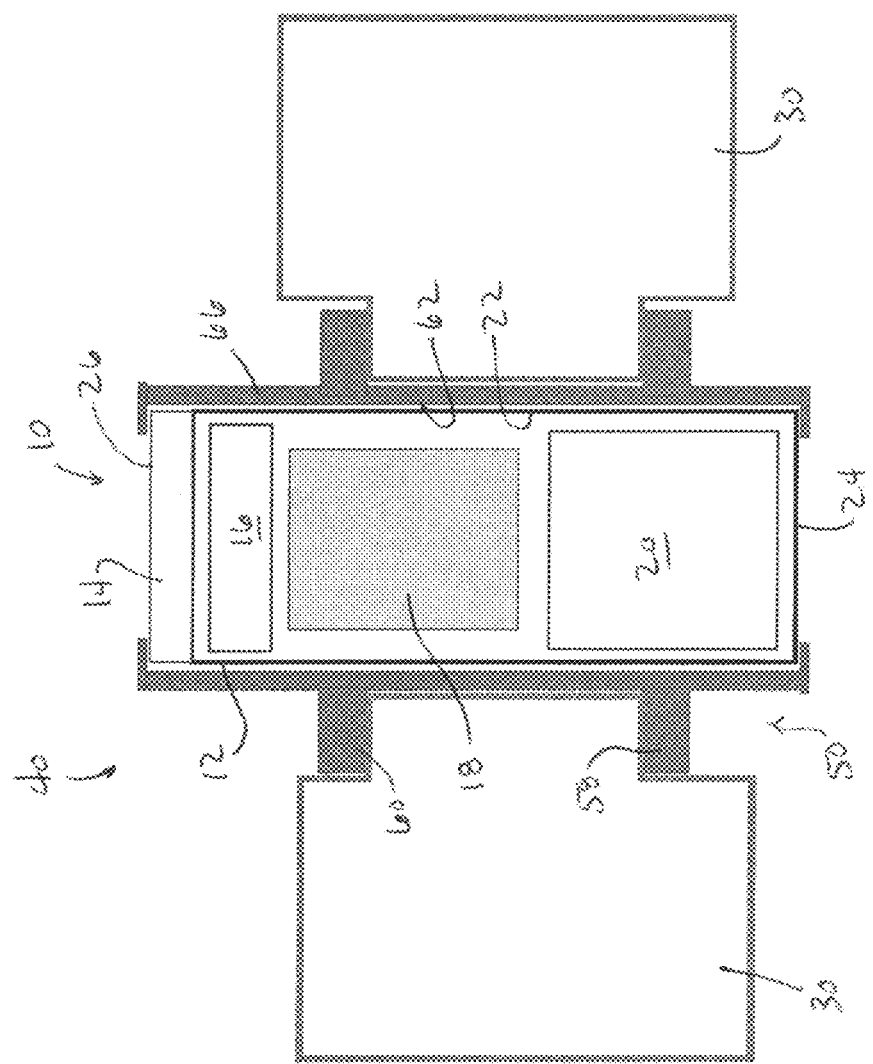

FIG. 19 represents a sensor assembly 40 in which the sensing device 10 of FIG. 7 assembled with a modified version of the anchor 50 of FIG. 5, in which the longitudinal legs 66 axially extend and protrude beyond both rings 58 and 60 of the anchor 50. The internal antenna 18 (located at the midsection of the housing 12) is predominantly (though not exclusively) surrounded or circumscribed by the longitudinal legs 66 that interconnect rings of the anchor 50. Similar to FIG. 17, though the rings 58 and 60 may be metallic, the legs 66 are preferably formed of a nonmetallic material so as to not have a Faraday-cage effect on the antenna 18.

FIG. 20 represents a sensor assembly 40 comprising the sensing device 10 of FIG. 10 assembled with the anchor 50 of FIG. 2, and shows the sensor assembly 40 implanted in a wall 30 of an organ with the anchor 50. The distal and proximal ends 24 and 26 of the sensing device 10 are located outside of the through-hole 62 of the anchor 50, which contacts and surrounds or circumscribes the region of the housing 12 formed by the additional housing portion 20 or otherwise in which the additional housing portion 20 is present and predominant. As a result, the external antenna 18 of the sensing device 10 is not surrounded or circumscribed by any portion of the anchor 50.

Figure 24:
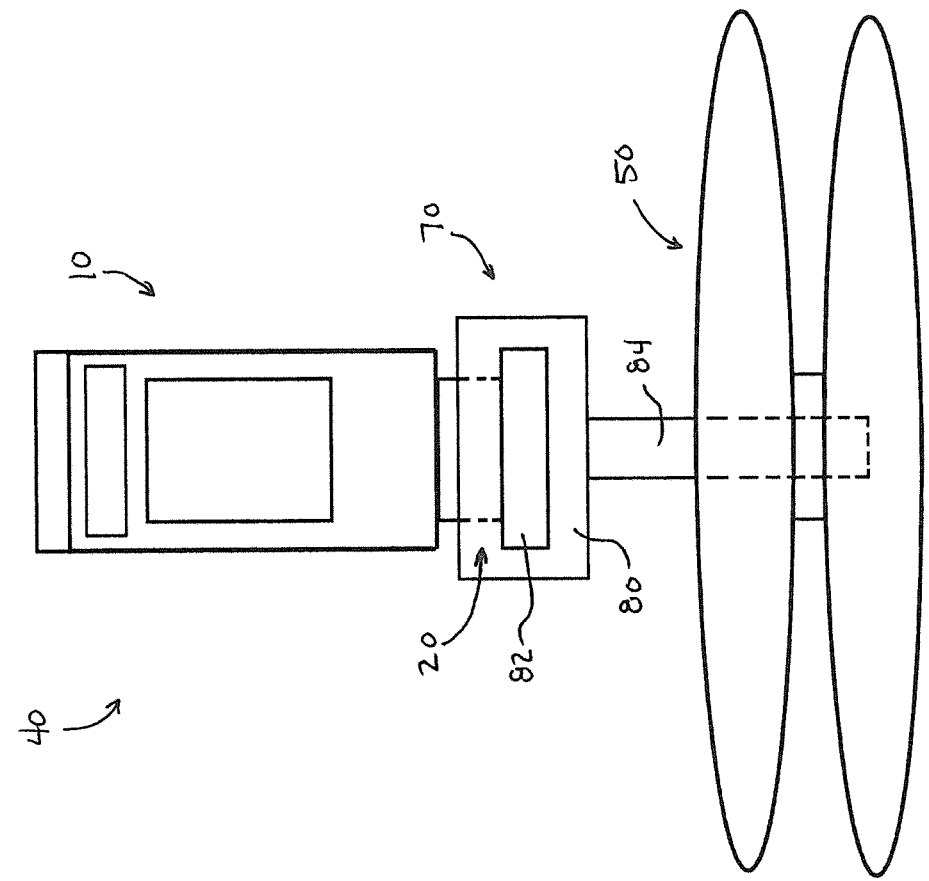
FIGS. 23 through 27 schematically represent various sensor assemblies comprising the sensing device of FIG. 21 and various different anchors or anchor interface members in accordance with nonlimiting aspects of the invention.
Figure 26:
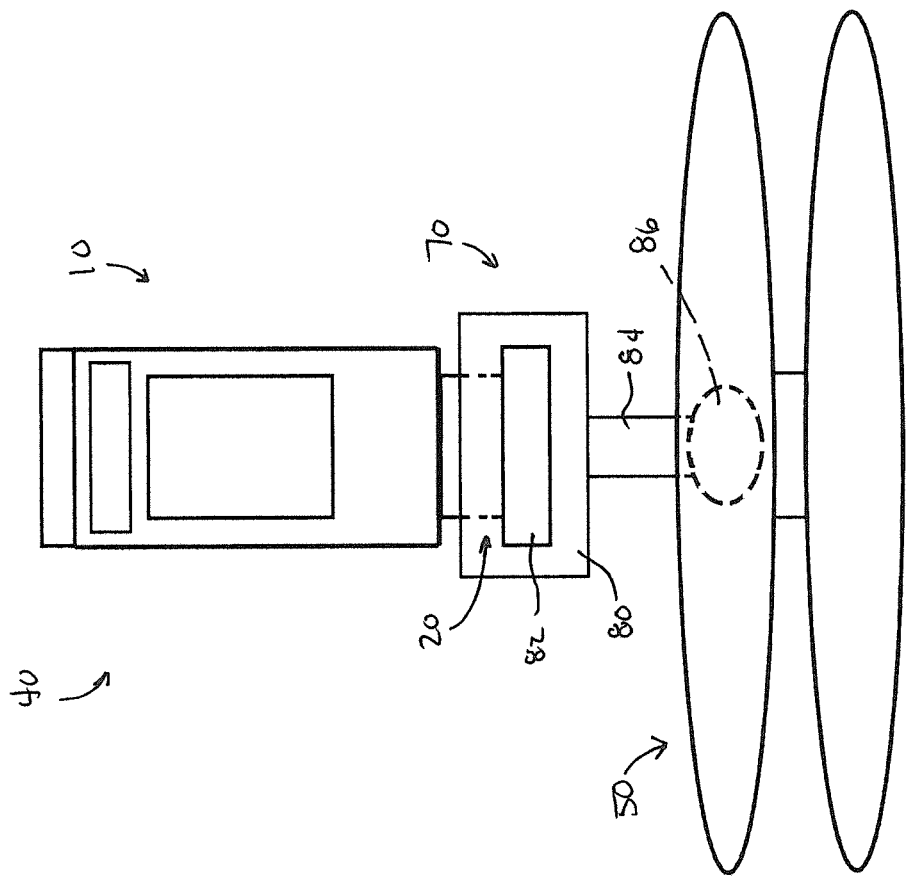

FIGS. 21 and 22 schematically represent additional embodiments of sensing devices 10 that comprise an additional housing portion 20 that is separately formed and directly attached to the distal end 24 of the sensing device housing 12 (FIG. 21) or integrally formed as a discrete region at the distal end 24 of the housing 12 (FIG. 22), but are otherwise similar in many respects to the sensing devices 10 discussed above. For example, the housings 12 of the sensing devices 10 are sized and shaped to accommodate the transducer 14, electronic circuitry 16, and antenna 18 within its internal cavity (or cavities) 22. Furthermore, the sensing devices 10 of FIGS. 21 and 22 include a housing portion 20 that is in addition to the internal cavity (or cavities) 22 that contain(s) the transducer 14, electronic circuitry 16, and antenna 18. The aforementioned housing portions 20 are sized and shaped for direct attachment to an anchor 50 or to an anchor interface member 70 (FIG. 23, 25, or 27) through which an anchor 50 can be coupled to the sensing devices 10 (FIGS. 24 and 26). As with the housing portions 20 described in reference to FIGS. 7 through 11, the housing portions 20 of FIGS. 21 and 22 are not required to contain any component relating to the operation of the sensing device 10 or its transducer 14, electronic circuitry 16, or antenna 18, and therefore a cavity is not required to be present in the additional housing portions 20. As such, the representations of the additional housing portions 20 in the drawings do not necessarily (though may) indicate a cavity, but instead more generally indicate a cavity-free solid. The housing portions 20 of FIGS. 21 and 22 are shown as extending from (FIG. 21) or defining (FIG. 22) the distal end 24 of their respective housings 12 and adjacent distal cavity regions 22A within the cavities 22 that do not contain any component relating to the operation of the sensing device 10 or its transducer 14, electronic circuitry 16, or antenna 18. As such, the housing portions 20 may be viewed as further encompassing the portion of their corresponding housing 12 in which the distal cavity regions 22A are located, though in the following discussion the housing portions 20 will be discussed as discrete portions of their respective sensing devices 10.

As previously noted, the housing portion 20 represented in FIG. 21 is a separately formed body that is then attached to the distal end 24 of the sensing device housing 12 by any suitable means, for example, an adhesive, fastener, metallurgical joint, mechanical clamping, thermal compression, etc., or combinations thereof. The housing portion 20 is configured to define an annular groove 72 surrounding a reduced portion 74 of the housing portion 20. The groove 72 and reduced portion 74 separate the distal end 24 of the housing 12 form an enlarged knob 76, which defines a proximal shoulder 78 facing the proximal end 26 of the housing 12. The groove 72, knob 76, and/or shoulder 78 provide coupling means (physical features) by which an anchor 50 or anchor interface member 70 may be coupled to the sensing device 10. The knob 76 may have various different shapes and cross-sectional shapes, including but not limited to spherical, disk, oval, rectangular, cubic, meander, wire, or combinations thereof. The diameter or lateral dimension of the knob 76 is shown as equal to that at the distal end 24 of the housing 12, though other diameters or lateral dimensions may be acceptable, depending on the particular anchor 50 or anchor interface member 70 to be coupled.

As also previously noted, the housing portion 20 represented in FIG. 22 is integrally formed as a discrete region of the housing 12 at its distal end 24. The housing portion 20 of FIG. 22 may (see phantom lines) but is not required to define an annular groove, and defines an enlarged knob 76 that defines a proximal shoulder 78 facing the proximal end 26 of the housing 12. The diameter or lateral dimension of the knob 76 is shown as greater than that of the housing 12 at its distal end 24, thereby providing coupling means (physical feature) by which an anchor 50 or anchor interface member 70 may be coupled to the sensing device 10.

The housing portions 20 represented in FIGS. 21 and 22 define knobs 76 and shoulders 78 and optional grooves 72 by which an anchor 50 or anchor interface member 70 may be coupled, though additional features are also foreseeable, for example, recesses, meander shapes or grooves, fastening features (e.g., threads), additional grooves, etc. In addition, the cross-sectional shapes of the housing portions 20 may be round, though other shapes are also foreseeable.

FIGS. 23 through 27 represent the sensing device 10 of FIG. 21 coupled to various anchors 50 and anchor interface members 70 through its housing portion 20. It should be understood that the sensing device 10 of FIG. 22 could be similarly coupled to the anchors 50 and interface members 70 through its housing portion 20. The anchors 50 and interface members 70 may be formed or fabricated from a variety of materials, including but not limited to metals including stainless steels and shape-memory alloys (e.g., NiTi alloys), polymers including PEEK, or combinations thereof.

Figure 23:
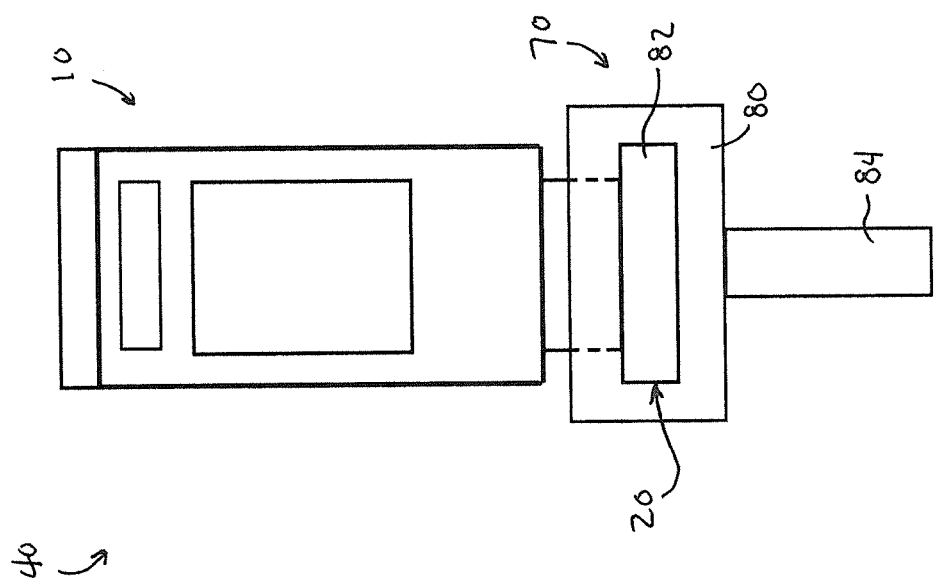
Figure 25:
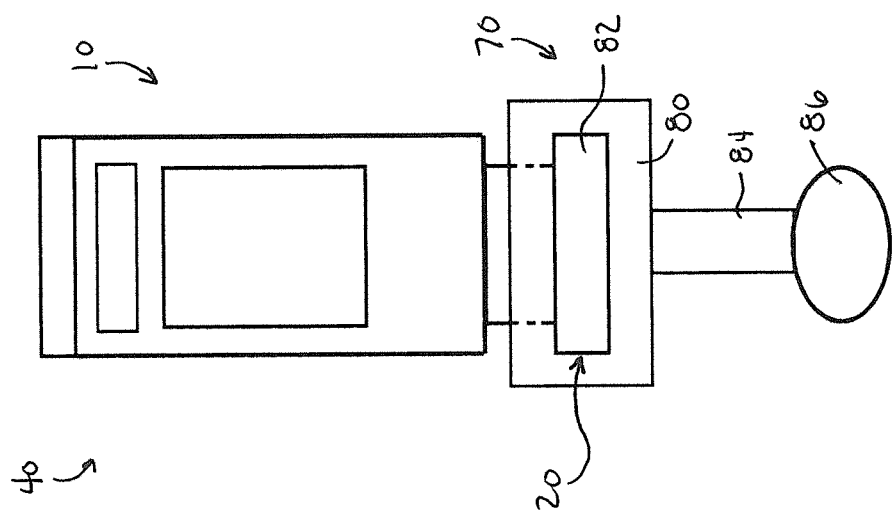
Figure 27:
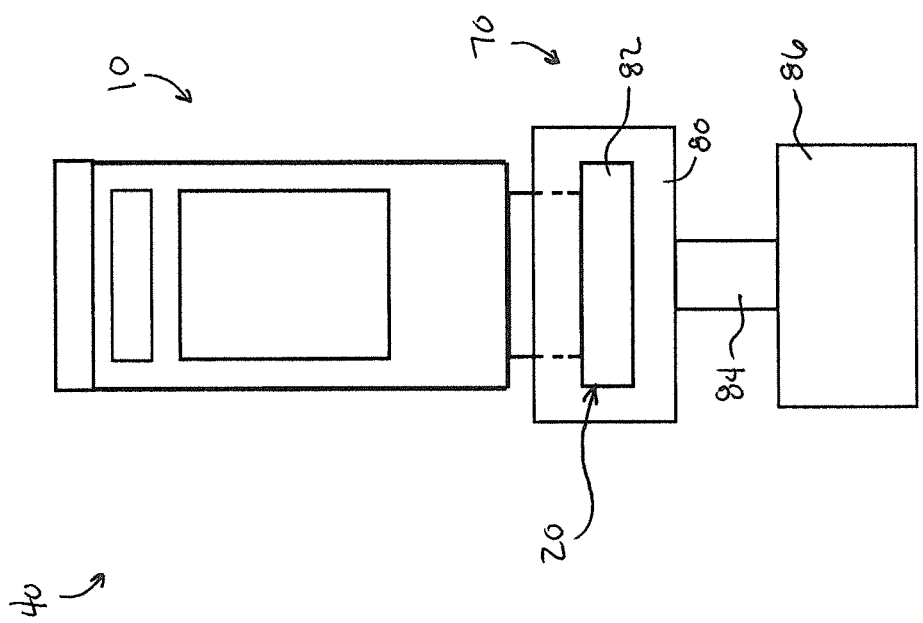

In FIGS. 23 and 24, the housing portion 20 of the device 10 is coupled to an interface member 70, which in turn serves to couple an anchor 50 to the device 10 to yield a sensor assembly 40. The interface member 70 comprises a head 80 having a cavity, recess, or groove 82 adapted to surround and grip the knob 76 of the housing portion 20. The interface member 70 further comprises a stem or post 84 that extends away from the device housing 12 along the longitudinal axis 28 of the housing 12. The post 84 is represented as having a continuous cross-sectional shape and size, and the anchor 50 is shown in FIG. 24 as surround a portion of the post 84 so as to be physically secured to the post 84, which may be by any suitable means, for example, an adhesive, fastener, metallurgical joint, mechanical clamping, thermal compression, etc., or combinations thereof. FIGS. 25, 26, and 27 depict embodiments that differ from that of FIGS. 23 and 24 by the inclusion of a knob 86 on the end of the post 84 of the interface member 70. The knob 86 has a larger cross-sectional shape than the post 84 to further facilitate the attachment of the anchor 50 and promote its retention on the sensing device 10. The knobs 86 are depicted in FIGS. 25, 26, and 27 as having either an ovoid or rectangular shape, though various other shapes and cross-sectional shapes are foreseeable, for example, spherical, disk, cubic, meander or wire-shaped, or combinations thereof. In some embodiments, the anchor 50 or interface device 70 (particularly its post 84 and knob 86) may be configured as a means for attaching and releasing the sensing device 10 with a delivery catheter. The anchor 50 may be, but is not limited to, anchors of types used as vascular closure devices, atrial septum defect occluder devices (ASD and PFO occluders), closure paravalvular leak devices, and other types of anchors.

As with other embodiments described herein, the housing portions 20 depicted in FIGS. 21 through 27 are particularly well suited for enabling a sensing device 10 to be secured with an anchor 50 such that the transducer 14 and antenna 18 of the sensing device 10 are sufficiently remote from the anchor 50 and anchor interface member 70 that any metallic portions thereof surround at least a portion of the housing portion 20 but do not surround the transducer 14 or antenna 18 and do not interfere with their operations. If the anchor 50 is configured as a vascular closure device, atrial septum defect occluder device (ASD or PFO occluder), or closure paravalvular leak device, the assembly 40 can be used as a closure or occluder device in addition to sensing a physiological parameter of a living being.

A notable advantage of sensor assemblies 40 of the types described above include the capability of effective long-term monitoring of the cardiovascular system and organs. Data obtained with the sensing devices 10 can be used for multiple purposes, including but limited to management of cardiac diseases, such as congestive heart failure, arrhythmia, structural heart diseases, congenital heart diseases, patients with single functioning ventricle, hypotension, hypertension, etc., and long-term management of patients. Data from the sensing devices 10 may be sampled at home, at a doctor's office, in a surgery room, during post-op stay including ICU, and during hospital stay.

Sensor assemblies 40 of the types represented in FIGS. 12 through 20, 24, and 26 can be implanted in various ways. For example, if implanted in an organ, one of the assemblies may be implanted in the wall 30 of the organ so that the proximal end 26 of the sensor housing 12 slightly protrudes into the organ, with the result that the sensor assembly 40 has little or no effect on blood flow through the organ. Alternatively, it is foreseeable that the entire sensor assembly 40 may be placed inside an organ, in which case an anchor 50 may be used to secure the sensing device 10 so that it is centrally located within the organ but is spaced apart from the walls 30 of the organ by legs or arms of the anchor 50 so as to have little if any effect on blood flow. For example, the anchor 50 can be equipped with one or more loops, fingers, spirals, screws, etc., that secure the sensing device 10 to oppositely-disposed walls 30 of the organ. Alternatively, the anchor 50 may be stitched to the wall 30 of the organ, such as with an anchor 50 disclosed in U.S. Pat. No. 9,168,005

The delivery of sensing devices and sensing assemblies of the types described above can be accomplished by percutaneous delivery, catheter delivery (preferably through the femoral vein), minimally invasive approaches, surgical approaches, or combinations thereof. The delivery procedure may be a standalone procedure or performed as part of another procedure.

While the invention has been described in terms of particular embodiments, it should be apparent that alternatives could be adopted by one skilled in the art. For example, the sensing devices 10, anchors 50, and sensor assemblies could differ in appearance and construction from the embodiments described herein and shown in the drawings, functions of certain components of the sensing devices 10, anchors 50, and sensor assemblies could be performed by components of different construction but capable of a similar (though not necessarily equivalent) function, and appropriate materials could be substituted for those noted. In addition, the invention encompasses additional or alternative embodiments in which one or more features or aspects of different disclosed embodiments may be combined. Accordingly, it should be understood that the invention is not necessarily limited to any embodiment described herein or illustrated in the drawings. It should also be understood that the phraseology and terminology employed above are for the purpose of describing the illustrated embodiments, and do not necessarily serve as limitations to the scope of the invention. Therefore, the scope of the invention is to be limited only by the following claims.

The invention claimed is:

1. A sensor assembly comprising:
   a sensing device comprising a housing having at least one internal cavity and a transducer and electrical circuitry within the at least one internal cavity, the sensing device further comprising an antenna that is within the at least one internal cavity or outside the housing, the transducer being located at a proximal end of the housing opposite a distal end of the housing;

at least one housing portion in which the transducer, the electrical circuitry, and the antenna are not located, the housing portion comprising coupling means that comprises a knob and a shoulder defined by the knob; and anchoring means that is discrete from the housing and the housing portion, the anchoring means comprising an anchor for securing the sensing device within a living body, the anchoring means being attached to the coupling means with the knob and/or the shoulder thereof so as to be coupled to and retained on the housing or the sensing device with the coupling means.

2. The sensor assembly of claim 1, wherein the coupling means of the housing portion comprises a groove in the housing portion that defines the knob and the shoulder.

3. The sensor assembly of claim 1, wherein the housing portion is separately formed and is attached to and extends from the distal end of the housing.

4. The sensor assembly of claim 1, wherein the housing portion is integrally formed as a discrete region of the housing.

5. The sensor assembly of claim 4, wherein the housing portion is located at and extends from the distal end of the sensor assembly or the housing.

6. The sensor assembly of claim 4, wherein the housing portion is located at a midsection of the sensor assembly or the housing.

7. The sensor assembly of claim 4, wherein the integral housing means is located at the proximal end of the sensor assembly or the housing.

8. The sensor assembly of claim 1, wherein the coupling means comprises a second knob for attaching and retaining the anchoring means to the housing or the sensing device.

9. The sensor assembly of claim 1, wherein the anchor means has a metal portion surrounding the coupling means of the housing portion but not surrounding the transducer or the antenna of the sensing device so that the metal portion is sufficiently remote from the transducer and the antenna to not interfere with operations thereof.

10. The sensor assembly of claim 1, wherein the anchoring means comprises:

an anchor interface member for securing the sensing device to the anchor, the anchor interface member having a first portion that surrounds the coupling means of the housing portion so as not to surround the transducer or the antenna.

11. The sensor assembly of claim 1, wherein the anchor is a vascular closure device, an atrial septum defect occluder device, or a closure paravalvular leak devices.

* * * * *